United States Patent
Sones

(10) Patent No.: US 7,313,270 B2
(45) Date of Patent: Dec. 25, 2007

(54) VISION SYSTEM AND METHOD FOR PROCESS MONITORING

(75) Inventor: Richard A. Sones, Cleveland, OH (US)

(73) Assignee: Applied Vision Company, LLC, Cuyahoga Falls, OH (US)

( * ) Notice: Subject to any disclaimer, the term of this patent is extended or adjusted under 35 U.S.C. 154(b) by 470 days.

(21) Appl. No.: 11/054,815

(22) Filed: Feb. 10, 2005

(65) Prior Publication Data

US 2005/0259868 A1    Nov. 24, 2005

Related U.S. Application Data

(63) Continuation-in-part of application No. 10/849,955, filed on May 19, 2004.

(51) Int. Cl.
  *G06K 9/62* (2006.01)
(52) U.S. Cl. .......... 382/159; 382/141; 382/218
(58) Field of Classification Search ........ 382/141–149, 382/159, 165, 218, 209; 348/92
  See application file for complete search history.

(56) References Cited

U.S. PATENT DOCUMENTS

| | | | | |
|---|---|---|---|---|
| 5,245,399 A | * | 9/1993 | Wertz et al. | ............ 356/71 |
| 5,754,448 A | | 5/1998 | Edge et al. | |
| 5,818,443 A | * | 10/1998 | Schott | ............ 382/141 |
| 5,835,244 A | | 11/1998 | Bestmann | |
| 5,911,003 A | * | 6/1999 | Sones | ............ 382/162 |
| 6,249,600 B1 | * | 6/2001 | Reed et al. | ............ 382/154 |
| 6,340,976 B1 | | 1/2002 | Oguchi et al. | |
| 6,459,425 B1 | | 10/2002 | Holub et al. | |
| 6,501,850 B2 | | 12/2002 | Setchell, Jr. | |
| 6,701,001 B1 | * | 3/2004 | Kenneway et al. | ............ 382/141 |
| 7,187,472 B2 | * | 3/2007 | Friedman et al. | ............ 358/1.9 |
| 2003/0179920 A1 | * | 9/2003 | Hooker et al. | ............ 382/141 |

OTHER PUBLICATIONS

Hardeberg, et al., "Multispectral image capture using a tunable filter," Ecole National Superieure des Telecommunications (Paris, France), May 2000.

* cited by examiner

*Primary Examiner*—Daniel Mariam
(74) *Attorney, Agent, or Firm*—Hahn Loeser & Parks, LLP; David J. Muzilla

(57) ABSTRACT

A method and system to monitor randomly oriented objects on a process line are disclosed. A color camera is used initially to collect a set of training images from a set of training objects on a process line. The training images represent various random spatial orientations of the training objects with respect to the color camera. The training objects serve as the standard for the process. The training images are stored in a computer-based platform. The color camera is then used to capture images of monitored objects as the monitored objects pass by the color camera on the process line. The monitored objects have a random spatial orientation with respect to the color camera as the monitored objects pass through the field-of-view of the color camera. The captured images of the monitored objects are processed by the computer-based platform and compared to the training images in order to determine if certain characteristic parameters of the monitored objects have deviated from those same characteristic parameters of the training objects. If so, the process may be adjusted to correct for the deviations in order to bring the process back into tolerance.

30 Claims, 14 Drawing Sheets

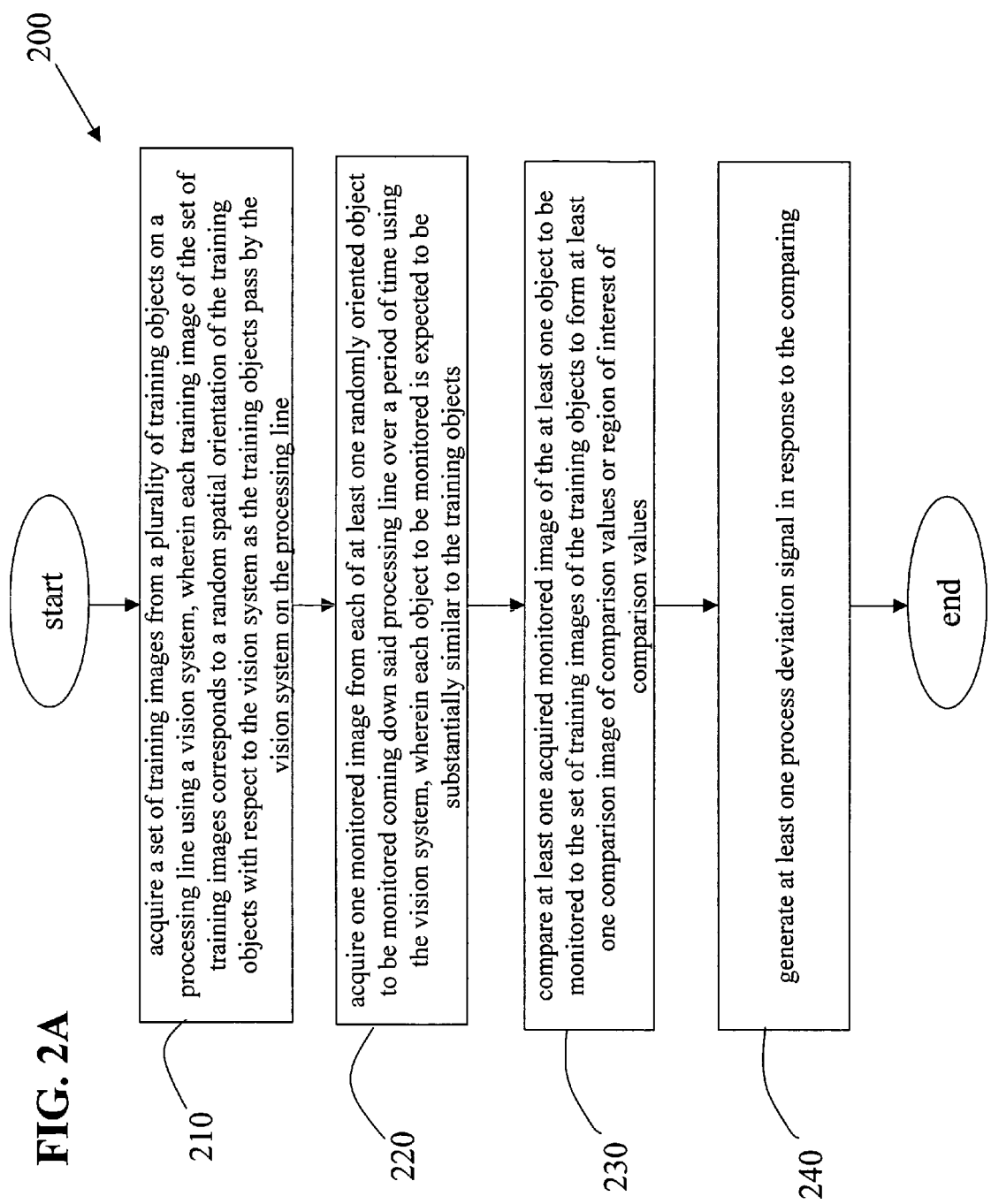

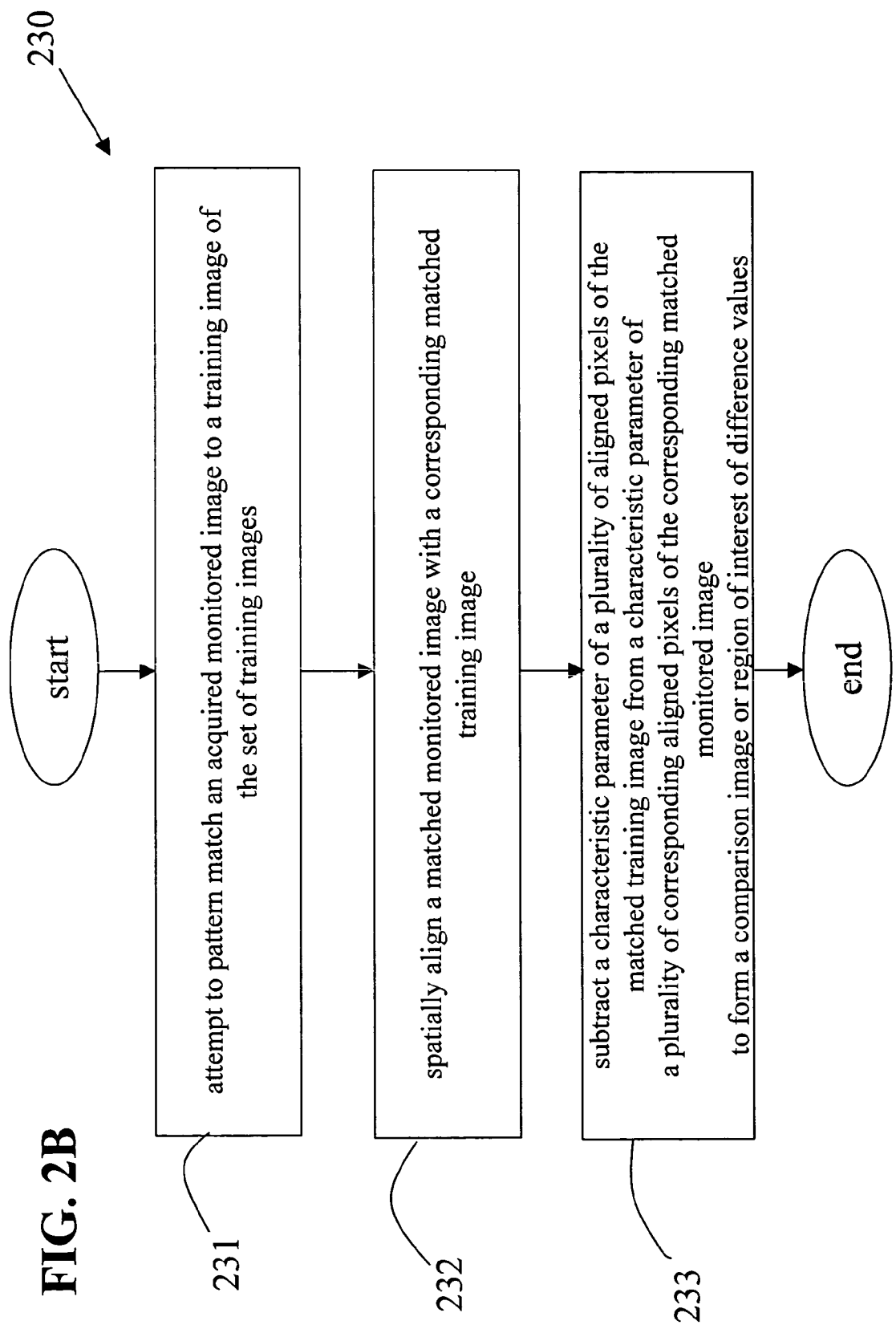

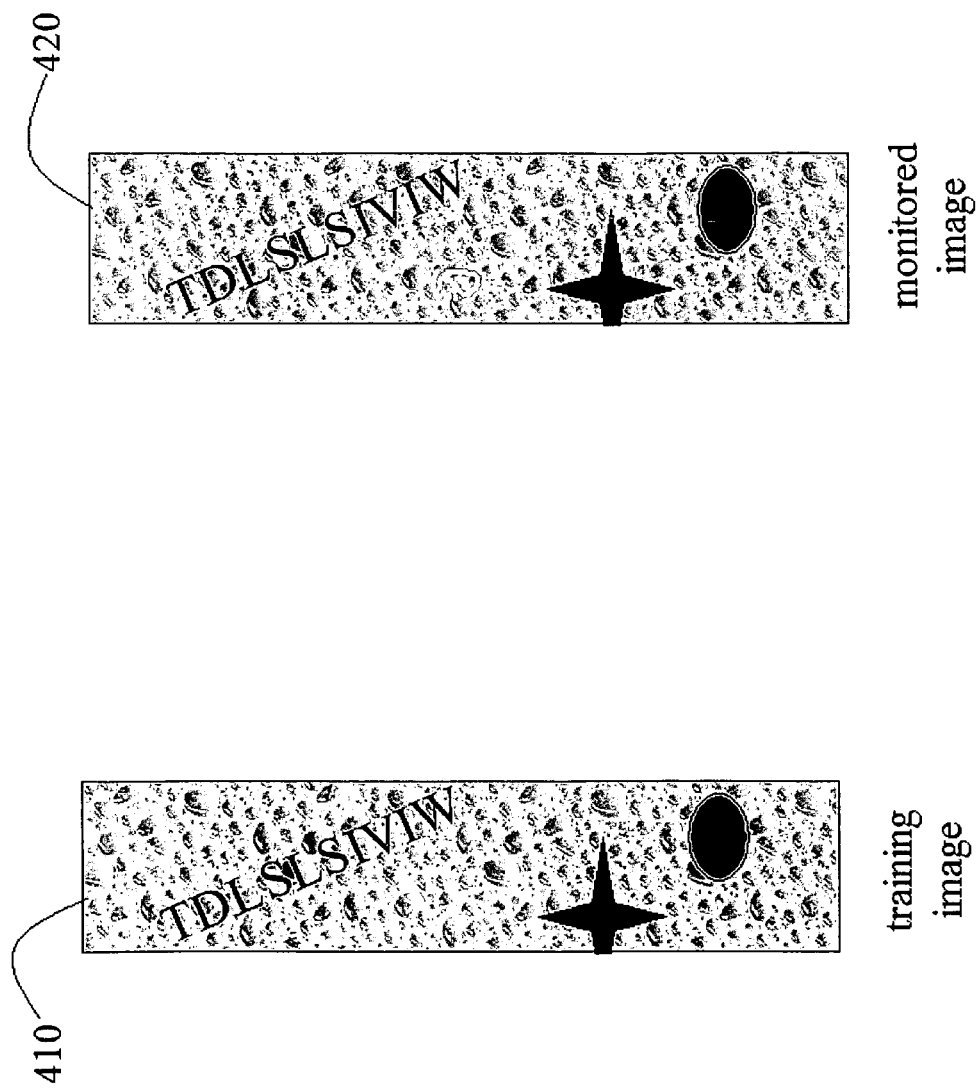

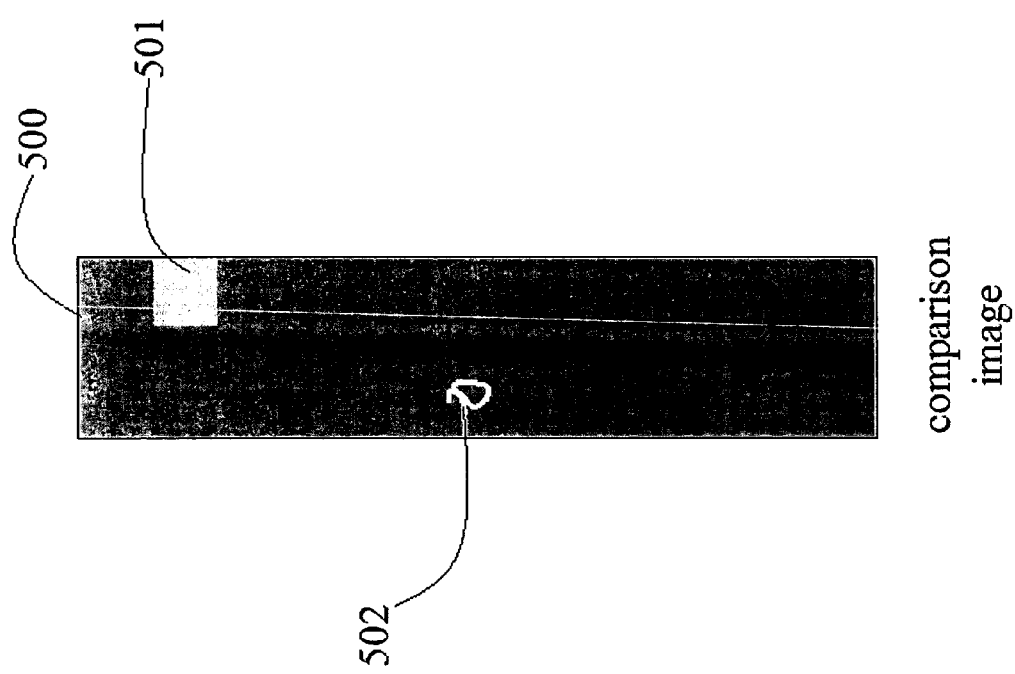

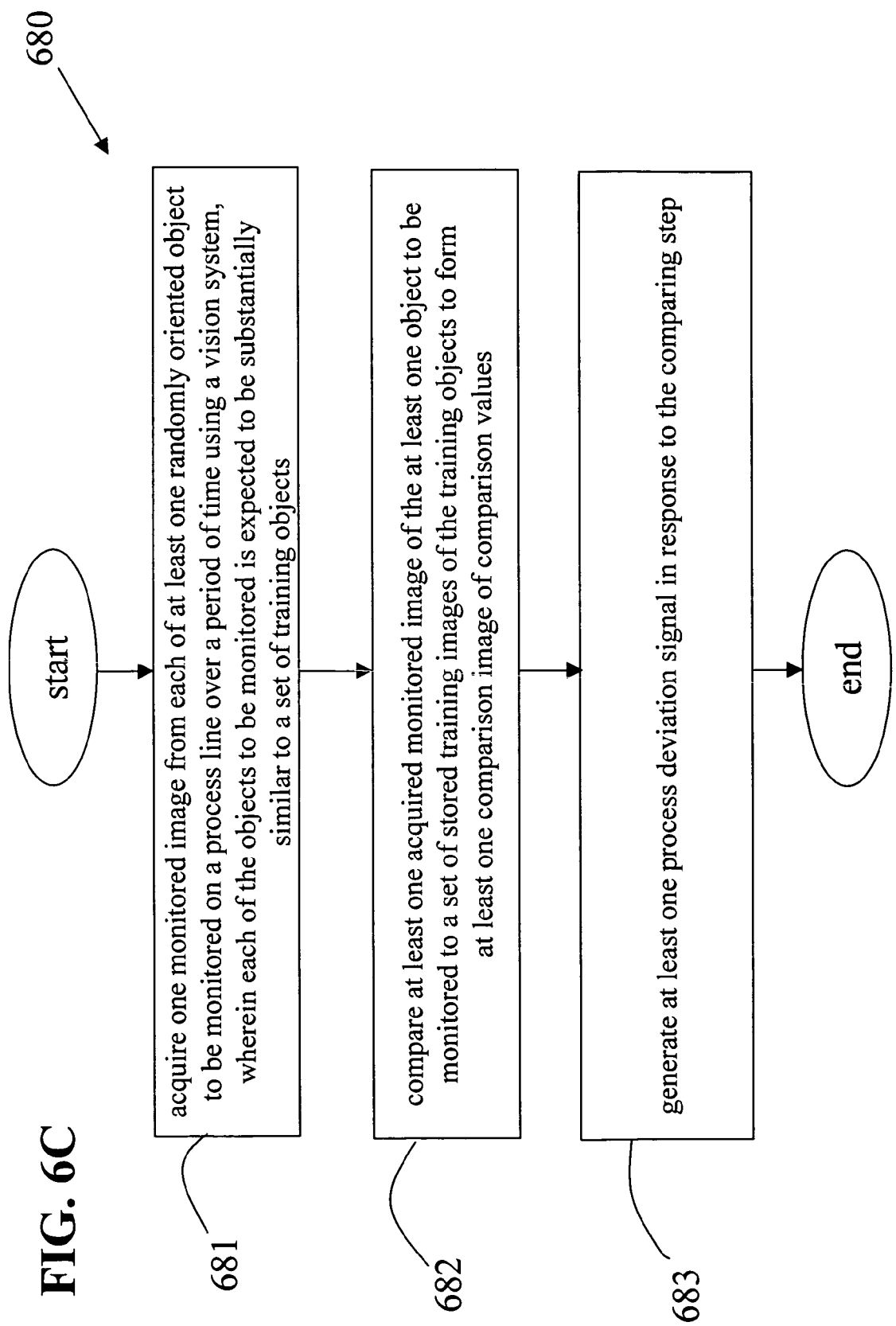

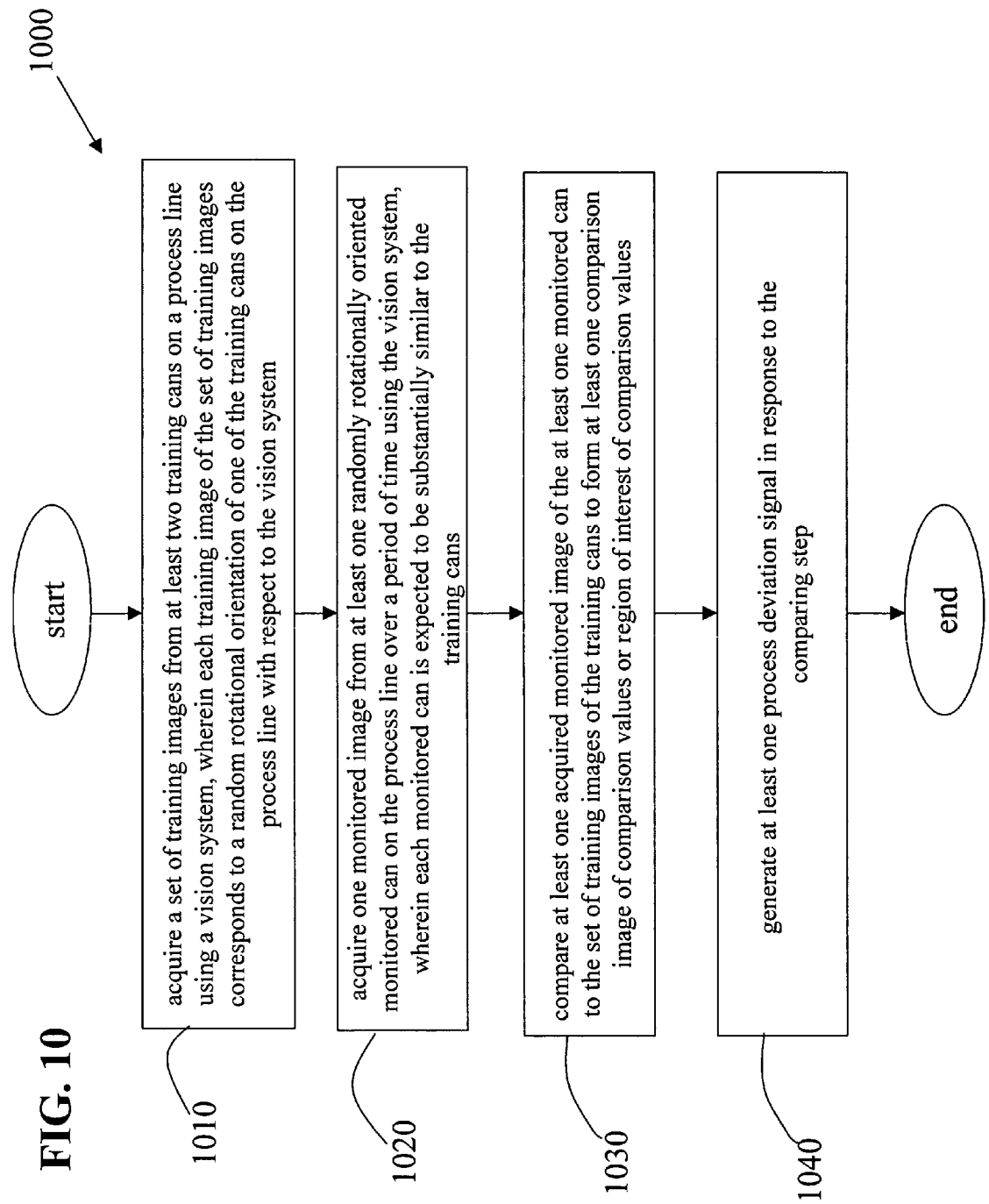

VISION SYSTEM AND METHOD FOR PROCESS MONITORING

CROSS-REFERENCE TO RELATED APPLICATIONS/INCORPORATION BY REFERENCE

This U.S. patent application is a continuation-in-part (CIP) of pending U.S. patent application Ser. No. 10/849,955 filed on May 19, 2004.

U.S. patent application Ser. No. 10/404,027, filed on Apr. 1, 2003, is incorporated herein by reference in its entirety. Also, U.S. patent application Ser. No. 10/411,741, filed on Apr. 10, 2003, is incorporated herein by reference in its entirety.

TECHNICAL FIELD

Certain embodiments of the present invention relate to training, process monitoring, and correction. More particularly, certain embodiments of the present invention relate to a vision system and method for monitoring a production line process in order to control certain characteristic parameters (e.g., absolute color) of monitored objects on the production line.

BACKGROUND OF THE INVENTION

Manufacturers of products that are produced in high volume as part of a process using, for example, a process line, employ quality assurance methods to ensure that certain features of the product (e.g., color, pattern, alignment, texture) are consistent and match a production reference standard. For example, in the soda can industry, the patterns and colors on the outer surface of the cans should be monitored somehow as the cans proceed down a process line to ensure that the process of printing the outer surface of the cans does not result in out of tolerance conditions (e.g., color drift, pattern alignment drift, etc.). The product moving down a process line is often spatially oriented in a random manner along the process line. For example, soda cans having a specific pattern printed on the cylindrical outer surface are typically oriented randomly about the vertical axis of rotation of the predominantly cylindrical can.

These methods can be as simple as a production floor operator performing a set-up of a product run by making visual comparison of a finished set-up part to a standard reference chart or reference part. Based on this comparison the operator makes adjustments to the process. Then another set-up part is created and compared, more adjustments made until acceptable results are achieved, and the product run is initiated. This subjective method may lead to errors because of differences in the ambient light conditions, positions of the inspection light source, and differences in surface textures between the reference part and the finished part, different people conducting the comparisons, and other factors. While such a subjective comparison may be appropriate for some manufacturing processes, other more sophisticated processes (e.g., multi-color processes) may require more objective techniques.

Examples of such processes include package printing processes, soda can printing processes, and other processes which may employ more complex color schemes that are repeated or are placed next to each other in use. Besides merely color concerns, these complex color schemes may have spatial or pattern defects. A trained quality assurance color inspector using a standard illuminant may be able to catch many of these defects by using a subjective comparison with a standard reference part, however, many of such defects may not be discernible to the naked eye. In such applications, manufacturers have typically used a color densitometer, a tristimulus colorimeter, or a reflectance spectrophotometer to provide more precise color matching by utilizing colorimetry, discussed in more detail below.

The process of quantitative color analysis is generally referred to as colorimetry. Since the introduction of the CIE (Commission International de l'Eclairage) color measurement system in the early 1930's, many different measurement systems have been proposed for different applications. One such measurement system is the CIE XYZ color space. The CIE XYZ color space characterizes colors by a luminance parameter Y and two color coordinates X and Z which specify the point on the chromaticity diagram. The XYZ parameters are based on the spectral power distribution of the light emitted from a colored object and are factored by sensitivity curves which have been measured for the human eye. The human eye has three different types of color-sensitive cones. Accordingly, the XYZ functions were intended to correspond to the average sensitivity of the human eye and provide a device-independent representation of color. Therefore, the spectral responses of the XYZ functions are known as "tristimulus" functions and make up the coordinate system to quantify a color image or color space.

The apparent color of an object depends not only on its intrinsic spectral reflectivity, but also on the spectrum of the light used to illuminate it. The CIE also has defined a number of standard illuminants which are defined, theoretically, in terms of their spectral content. To completely specify the color of an object, one must measure the XYZ values of the light emanating from the object when it is illuminated by a standard illuminant.

Another CIE color space which is frequently used is the L*a*b* color space. The values of L*, a*, and b* are derived mathematically from the tristimulus values of X, Y, and Z:

$$L^* = 116\left(\frac{Y}{Y_n}\right)^{1/3} - 16$$

$$a^* = 500\left[\left(\frac{X}{X_n}\right)^{1/3} - \left(\frac{Y}{Y_n}\right)^{1/3}\right]$$

$$b^* = 200\left[\left(\frac{Y}{Y_n}\right)^{1/3} - \left(\frac{Z}{Z_n}\right)^{1/3}\right]$$

where the values with the subscript "n" are found in published tables and correspond to a chosen standard illuminant. The value of L* is proportional to the brightness (luminosity) of the color. The value of a* describes the red/green composition of the color. The value of b* describes the yellow/blue composition of the color.

The goal of the L*a*b* color space is to provide a color space where the Euclidean distance between color 1 and color 2

$$\Delta E = \sqrt{(\Delta L^*)^2 + (\Delta a^*)^2 + (\Delta b^*)^2}$$

wherein:
$\Delta L^* = L_1^* - L_2^*$
$\Delta a^* = a_1^* - a_2^*$
$\Delta b^* = b_1^* - b_2^*$ is a "perceptually uniform" measure of the difference between color 1 and color 2. A value of $\Delta E = 1$ corresponds to a color difference which is very subtle—so subtle that it would take a trained color observer working under ideal lighting conditions to notice the difference. A value of $\Delta E=2$ corresponds to a difference in color which is twice as noticeable as $\Delta E=1$, and so on. The "perceptual distance" denoted by a given value of $\Delta E$ is intended to be independent of the location in color space (that is, independent of hue, saturation, and brightness), but this independence is actually only an approximation. Regardless, $\Delta E$ has been accepted in the color industry to quantify color differences.

As stated above, manufacturers typically have used a tristimulus calorimeter, a reflectance spectrophotometer, or a color densitometer to provide more precise color matching by utilizing one or more color measurement systems. These instruments provide quantitative and objective feedback, but are slow and inconvenient, and only measure color at one small spot (typically 5 mm in diameter) at a time, making it inconvenient to impossible to use them to compare all the colors on a complex multi-color pattern. Many colorimeters have to touch the object to get a reading. When trying to do colorimetry on a complex pattern, it is difficult to get the sampling region always in the same spot with respect to the pattern. In addition, these devices tend to be expensive due to the manufacturing care necessary to construct a device capable of providing precise color measurements suitable for laboratory use. These disadvantages make these devices particularly unsuitable for the production floor for use in process control.

Another disadvantage with densitometers is that they do not provide absolute color metrics (such as XYZ tristimulous values). Instead, they report the overall reflectivity of a surface for red, green, and blue light. Color densitometers are only suited for relative (as opposed to absolute) measurements. These relative measurements are often sufficient when the goal is simply to determine if the color on one object "matches" the color on another object.

Therefore there remains a need in the art for a fast and convenient way to efficiently monitor a production process with respect to a standard reference, where the production objects being monitored may have a random spatial orientation, at least around one axis.

Further limitations and disadvantages of conventional, traditional, and proposed approaches will become apparent to one of skill in the art, through comparison of such systems and methods with the present invention as set forth in the remainder of the present application with reference to the drawings.

BRIEF SUMMARY OF THE INVENTION

An embodiment of the present invention comprises a method for training and monitoring a process. The method includes acquiring a set of training images from a plurality of training objects on a processing line using a vision system. Each training image of the set of training images corresponds to a random spatial orientation of the training objects with respect to the vision system as the training objects pass by the vision system on the processing line. The method further includes acquiring one monitored image from each of at least one randomly oriented object to be monitored coming down the processing line over a period of time using the vision system. Each object to be monitored is expected to be substantially similar to the training objects. The method also includes comparing at least one acquired monitored image of the at least one object to be monitored to the set of training images of the training objects to form at least one comparison image of comparison values or region of interest of comparison values. The method further includes generating at least one process deviation signal in response to the comparing step.

Another embodiment of the present invention comprises a vision system for monitoring a process. The vision system comprises a source of illumination positioned to illuminate objects for training and objects to be monitored as the training objects and the objects to be monitored move along a process line in spatially random orientations. The system further includes a color camera positioned on the process line to capture at least one image from each of the illuminated training objects and each of the illuminated objects to be monitored, forming a plurality of training images and a plurality of monitored images, as each training object and each object to be monitored passes through a field-of-view of the color camera. The system also includes a computer-based platform being connected to the color camera to store the plurality of training images and the plurality of monitored images and to generate at least one process deviation signal by comparing at least one monitored image of the plurality of monitored images to the plurality of training images.

A further embodiment of the present invention comprises a method for training and monitoring a process. The method includes generating a set of training images from a plurality of training objects on a product line using a vision system. Each training image of the set of training images corresponds to a random spatial orientation of each of the training objects on the product line with respect to the vision system. The method further includes acquiring one monitored image from each of at least one randomly oriented object to be monitored on the product line over a period of time using the vision system. Each object to be monitored is expected to be substantially similar to the training objects. The method also includes comparing at least one acquired monitored image for the at least one object to be monitored to the set of training images of the training objects to form at least one process deviation signal.

Another embodiment of the present invention comprises a method of monitoring a process. The method includes acquiring one monitored image from each of at least one randomly oriented object to be monitored on a process line over a period of time using a vision system. Each object to be monitored is expected to be substantially similar to a set of training objects. The method further includes comparing at least one acquired monitored image of the at least one object to be monitored to a set of stored training images of the training objects to form at least one comparison image of comparison values. The method also includes generating at least one process deviation signal in response to the comparing step.

A further embodiment of the present invention comprises a method of training a vision system. The method includes running a set of training objects down a product processing line and illuminating the training objects, one at a time, on the product processing line using a source of illumination. The method further includes collecting a set of training images of the training objects with a color camera as the training objects pass the color camera on the product processing line. Each training image of the set of training images corresponds to a random spatial orientation of one of the training objects with respect to the color camera. The method also includes processing and storing the set of training images using a computer-based platform which is connected to the color camera.

Another embodiment of the present invention comprises a method for training and monitoring an industrial can or container process. The method includes acquiring a set of training images from at least two training cans on a process line using a vision system. Each training image of the set of training images corresponds to a random rotational orientation of one of the training cans on the process line with respect to the vision system. The method further includes acquiring one monitored image from at least one randomly rotationally oriented monitored can on the process line over a period of time using the vision system. Each monitored can is expected to be substantially similar to the training cans. The method also includes comparing at least one acquired monitored image of the at least one monitored can to the set of training images of the training cans to form at least one comparison image of comparison values or region of interest of comparison values. The method further includes generating at least one process deviation signal in response to the comparing.

These and other advantages and novel features of the present invention, as well as details of an illustrated embodiment thereof, will be more fully understood from the following description and drawings.

BRIEF DESCRIPTION OF SEVERAL VIEWS OF THE DRAWINGS

FIG. 2A illustrates a flowchart of a first embodiment of a method to train and monitor a process using the vision system of FIG. 1, in accordance with various aspects of the present invention.

FIG. 2B illustrates a flowchart of an embodiment of a comparison step performed in the method of FIG. 2A, in accordance with various aspects of the present invention.

FIG. 4 illustrates an exemplary training image which is to be compared to an exemplary monitored image, in accordance with the method of FIGS. 2A-2B.

FIG. 5 illustrates an exemplary comparison image generated by subtracting the training image of FIG. 4 from the monitored image of FIG. 4, in accordance with the method of FIGS. 2A-2B.

FIG. 6C is a flowchart of an embodiment of a method to monitor a process, in accordance with various aspects of the present invention.

FIG. 10 is a flowchart of an embodiment of a method for training and monitoring an industrial can or container process, in accordance with various aspects of the present invention.

DETAILED DESCRIPTION OF THE INVENTION

Figure 1:
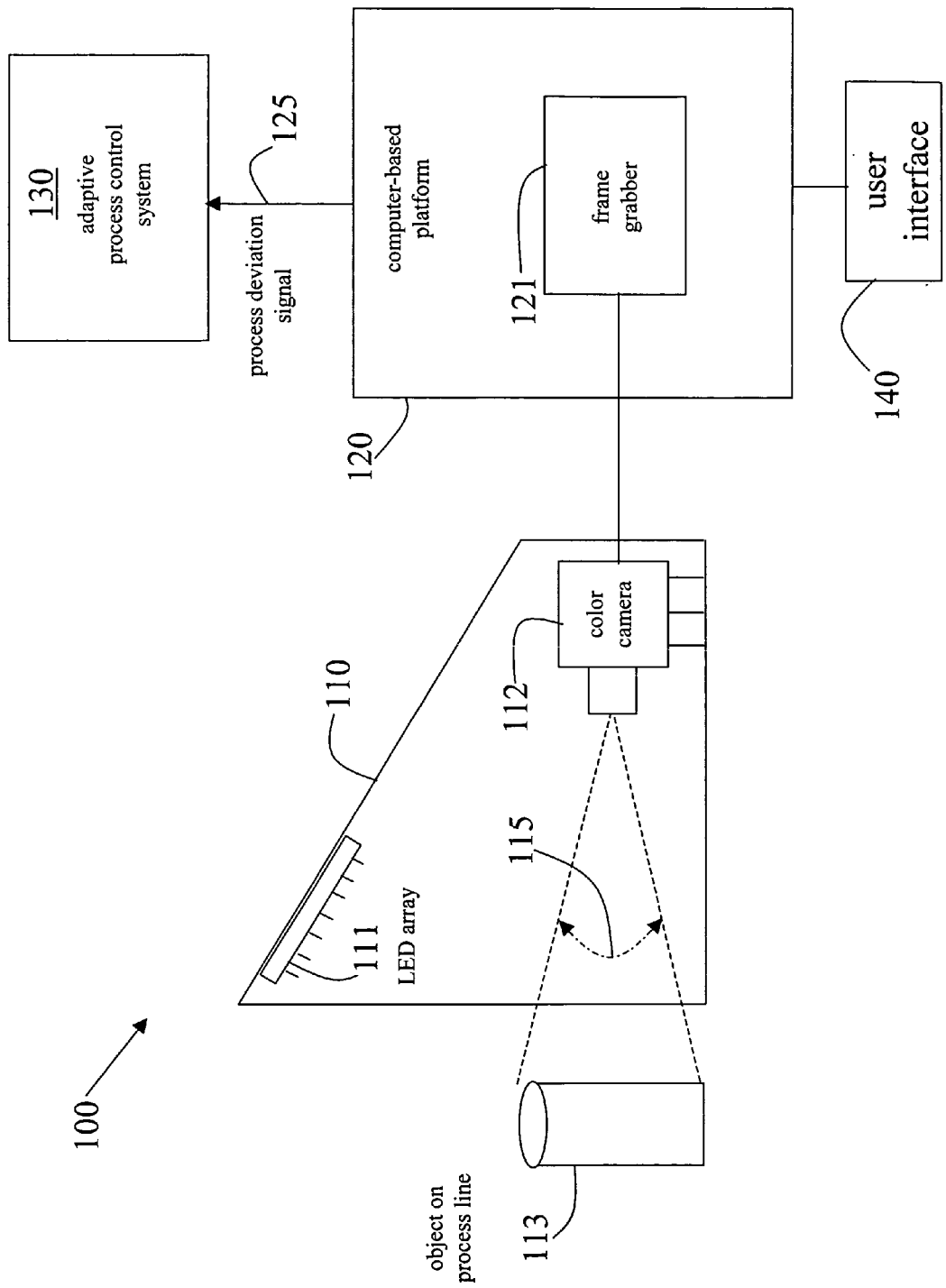
FIG. 1 illustrates an embodiment of a vision system for training and monitoring a process, in accordance with various aspects of the present invention.

FIG. 1 illustrates an embodiment of a vision system 100 for training and monitoring a process, in accordance with various aspects of the present invention. The process may be continuously monitored in real-time or periodically, in accordance with various aspects of the present invention. The vision system 100 includes an imaging assembly 110 which includes a source of illumination 111 and a color camera 112 to collect images of training objects and objects to be monitored 113 on a process line. The vision system 100 also includes a computer-based platform 120 connected to the color camera 112 in order to store and process image data (e.g., characteristic parameter data) collected by the color camera 112 from the training objects or objects to be monitored 113 on the process line.

In accordance with an embodiment of the present invention, the computer-based platform 120 comprises a standard, commercial, off-the-shelf personal computer (PC) running a general purpose operating system. However, the computer-based platform 120 also includes image processing software tools which may be commercially available and/or customized software. In accordance with an embodiment of the present invention, the computer-based platform 120 also provides control signals to the color camera 112 in order to control certain functionality of the color camera 112 (e.g., focusing and image capture rate).

In accordance with an embodiment of the present invention, the color camera 112 outputs analog imaging signals and the computer-based platform 120 includes a frame grabber 121 to convert the analog imaging signals to frames of digital imaging data. In accordance with another embodiment of the present invention, the color camera 112 outputs digital imaging signals directly and the frame grabber 121 is not used. The color camera 112 comprises a three-color camera providing RGB (red, green, blue) color imaging signals. In accordance with an alternative embodiment of the present invention, the camera 112 comprises a gray scale or monochrome camera.

The imaging assembly 110 is positioned (i.e., mounted) on a product processing line such that a portion of the objects 113 (e.g., printed soda cans) moving past (e.g., on a conveyor system) the imaging assembly 110 on the processing line and facing the color camera 112 may be imaged by the color camera 112 while being illuminated by the source of illumination 111. In accordance with an embodiment of the present invention, the source of illumination 111 comprises an array of light emitting diodes (LEDs) having a white light spectrum. Such a white light spectrum is useful for determining the true colors of the monitored object. The objects on a typical product processing line pass by the imaging assembly 110 at a rate of about 1800 objects per minute. Other rates are possible as well.

The vision system 100 may also include a user interface 140 including a display which may be used by an operator to view images and to control the vision system 100 via, for example, a menu-driven touch-screen display. The user interface connects to the computer-based platform 120.

In use, the vision system 100 captures color images of training objects 113 (e.g., a substantially cylindrical can with printed graphics and text on its outer surface) as the training objects 113 pass by the vision system 100 on the production process line. The training objects 113 represents an ideal standard of the objects to be monitored on a production process line. The production process line may be, for example, a soda can printing line for printing the outer surface of soda cans at a rapid pace. Cans used for training are simply the cans coming down the product process line by the vision system once the operator of the vision system is happy with the product (i.e., soda cans) currently coming down the line (e.g., once the printed cans have satisfied the operator, then train). The vision system then makes sure the process (e.g., printing process) does not drift too far away from the training set.

In accordance with one embodiment of the present invention, sixteen training images are collected from sixteen training objects using the color camera 120 such that each of the sixteen training images correspond to a random vertical segment or strip of the outer surface of a training object. That is, each of the sixteen training images correspond to a random rotational position of a training object with respect to the field-of-view 115 of the color camera 112 as the training object moves through the field-of-view of the color camera on the process line. The training images are transferred to and digitally stored in the computer-based platform 120 as arrays of pixel data (e.g., RGB color values).

In accordance with an embodiment of the present invention, the training images are processed by the computer-based platform 120 to correct for lighting non-uniformity due to variations in the source of illumination 111 and/or due to the spatial relationship between the source of illumination 111, the training object 113, and the color camera 112. A white reference image may initially be used with a brightness reference strip to calibrate the vision system 100 such that training images of true training objects (e.g., soda cans) can be corrected for lighting non-uniformity. The training images will be used in the vision system to compare monitored images from monitored objects on a processing line to the training images in order to ensure process control. Acquiring and processing the training images is referred to herein as "on-line training" since the training images are captured from the same process line that will be monitored. An advantage of "on-line" training is that the exact same vision system and set-up (i.e., geometry, lighting, etc.) is being used to both train and monitor on the same process line.

FIG. 2A illustrates a flowchart of a first embodiment of a method 200 to train and monitor a process using the vision system 100 of FIG. 1, in accordance with various aspects of the present invention. In step 210, a set of training images is acquired from a plurality of training objects on a processing line using a vision system. Each training image of the set of training images corresponds to a random spatial orientation of the training objects with respect to the vision system as the training objects pass by the vision system on the processing line. In step 220, one monitored image is acquired from each of at least one randomly oriented object to be monitored coming down the processing line over a period of time using the vision system. Each object to be monitored is expected to be substantially similar to the training objects. In step 230, at least one acquired monitored image of the at least one object to be monitored is compared to the set of training images of the training objects to form at least one comparison image of comparison values or region of interest of comparison values. In step 240, at least one process deviation signal is generated in response to the comparison step 230. Steps 230 and 240 are performed by, for example, the computer-based platform 120.

FIG. 2B illustrates a flowchart of an embodiment of the comparison step 230 performed in the method 200 of FIG. 2A, in accordance with various aspects of the present invention. In step 231, an attempt is made to pattern match an acquired monitored image to a training image of the set of training images. All of the training images are tried, one at a time, to determine a best match to the monitored image. A confidence measure is generated for each training image to determine which training image provides the best match to the monitored image. If the resultant confidence measure for each training image is below a certain predetermined value, then no match is accomplished and the monitored image is not used further in the monitoring process. In step 232, a matched monitored image is spatially aligned with a corresponding matched training image. In step 233, a characteristic parameter (e.g., a RGB color value) of each aligned pixel of the matched training image is subtracted from a characteristic parameter of each corresponding aligned pixel of the corresponding matched monitored image to form a comparison image of difference values. In step 240, the process deviation signal is generated from the comparison image of difference values (see FIG. 2A). The method 200 is performed for each monitored image acquired by the vision system 100.

In accordance with an alternative embodiment of the present invention, only a subset of pixels corresponding to a region-of-interest (ROI) of the matched images may be compared, thus reducing the amount of computational operations required to complete the comparison, or simply to focus on a part of the object requiring more sensitive inspection. The ROI may comprise, for example, a disk-shaped area, a square area, a rectangular area, or some other shaped area.

During monitoring, about $\frac{1}{8}^{th}$ of the soda can is acquired as an image to increase the probability of determining a match since each training image corresponds to about $\frac{1}{16}^{th}$ of the soda can, in accordance with an embodiment of the present invention.

The characteristic parameter may comprise, for example, RGB color data for qualitative comparisons (e.g., looking for printing flaws on a soda can), or absolute colorimetric data such as XYZ color data or L*a*b* color data for true color comparisons. As a result, the comparison image of difference values may comprise, for example, $\Delta R \Delta G \Delta B$ values, $\Delta X \Delta Y \Delta Z$ colorimetric values, $\Delta L^* \Delta a^* \Delta b^*$ colorimetric values, or $\Delta E$ calorimetric values. Typically, for qualitative colorimetric comparisons, only selected regions-of-interest (ROI) of the images are compared to cut down on the amount of processing.

As an example, the pixel data may comprise RGB values from the three-color camera 112. These RGB values may be used directly to form the comparison image by subtracting the RGB pixel values of the matched training image from the RGB pixel values of the matched monitored image. In this way, qualitative differences can be ascertained from the comparison image.

Figure 3A:
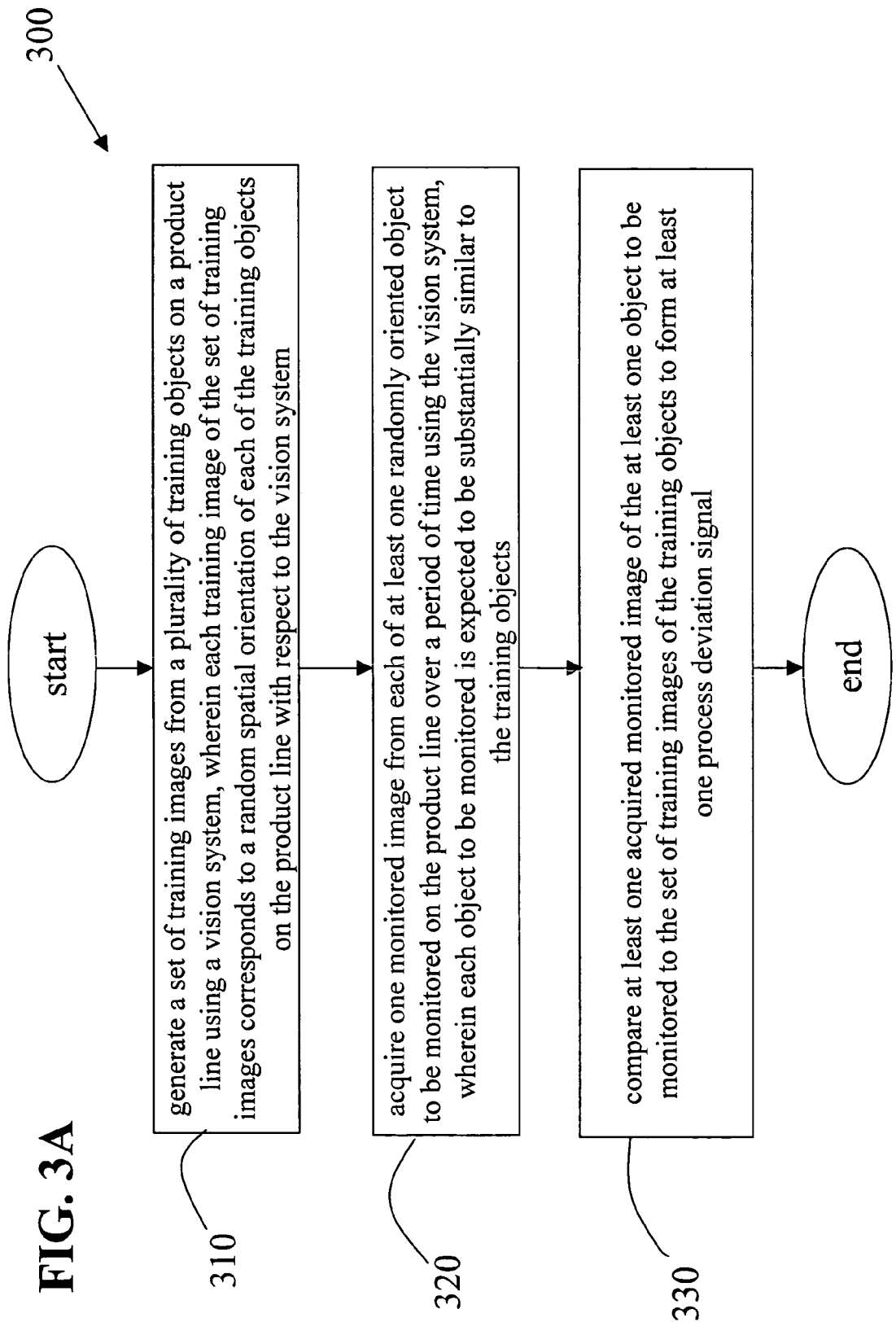
FIG. 3A illustrates a flowchart of a second embodiment of a method for training and monitoring a process, in accordance with various aspects of the present invention.

FIG. 3A illustrates a flowchart of a second embodiment of a method 300 for training and monitoring a process, in accordance with various aspects of the present invention. In step 310, a set of training images is generated from a plurality of training objects on a product line using a vision system. Each training image of the set of training images corresponds to a random spatial orientation of each of the training objects on the product line with respect to the vision system. In step 320, one monitored image is acquired from each of at least one randomly oriented object to be monitored on the product line over a period of time using the vision system. Each object to be monitored is expected to be substantially similar to the training objects. In step 330, at least one acquired monitored image of the at least one object to be monitored is compared to the set of training images of the training objects to form at least one process deviation signal. Such a method 300 is not concerned with generating a comparison image but, instead, is directed to generating a process deviation signal for the purpose of, for example, performing comparisons of absolute color over a region of interest.

Figure 3B:
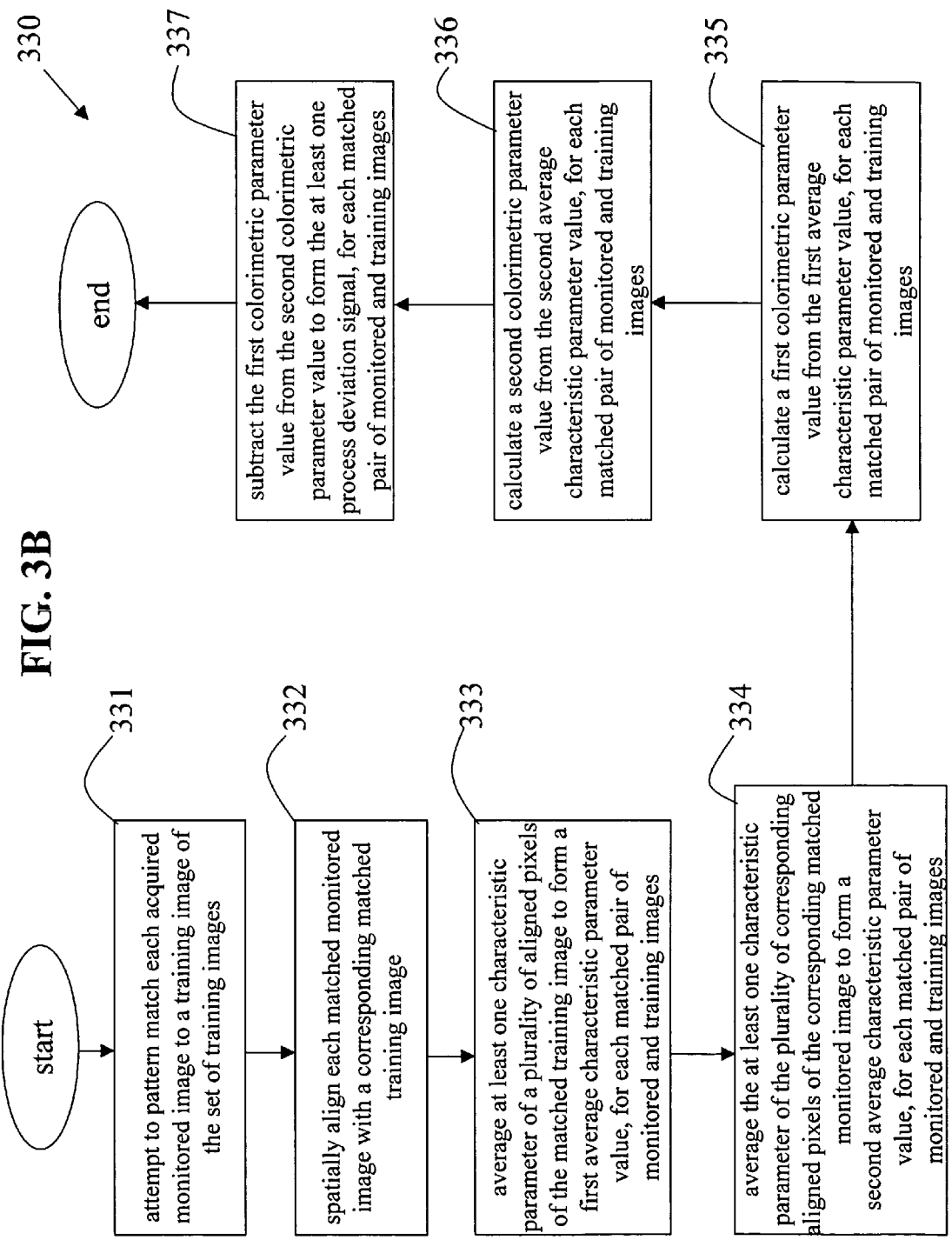
FIG. 3B illustrates a flowchart of an embodiment of a comparison step performed in the method of FIG. 3A, in accordance with various aspects of the present invention.

FIG. 3B illustrates a flowchart of an embodiment of a comparison step 330 performed in the method of FIG. 3A, in accordance with various aspects of the present invention. In step 331, an attempt is made to pattern match each acquired monitored image to a training image of the set of training images. In step 332, each matched monitored image is spatially aligned with a corresponding matched training image. In step 333, at least one characteristic parameter of a plurality of aligned pixels of the matched training image is averaged to form a first average characteristic parameter value, for each matched pair of monitored and training images. In step 334, at least one characteristic parameter of the plurality of corresponding aligned pixels of the corresponding matched monitored image is averaged to form a second average characteristic parameter value, for each matched pair of monitored and training images. In step 335, a first calorimetric parameter value is calculated from the first average characteristic parameter value, for each matched pair of monitored and training images. In step 336, a second colorimetric parameter value is calculated from the second average characteristic parameter value, for each matched pair of monitored and training images. In step 337, the first calorimetric parameter value is subtracted from the second calorimetric parameter value to form at least one process deviation signal, for each matched pair of monitored and training images.

For example, for colorimetric comparisons, RGB pixel values (corrected for lighting variations) are averaged and converted to XYZ or L*a*b* colorimetric values for a predetermined ROI of the matched pair of training and monitored images. Multiple RGB pixels are averaged and then the calorimetric values are generated using a color transformation algorithm. The averaging helps reduce noise that is present in the original RGB data. As a result, a single colorimetric value is determined for the ROI of the training image and a single calorimetric value is determined for the corresponding aligned ROI of the monitored image.

Next, the single calorimetric value for the predetermined region-of-interest (ROI) of the matched training image is subtracted from the single calorimetric value for the corresponding aligned ROI of the matched monitored image, forming a $\Delta X \Delta Y \Delta Z$ or $\Delta L^* \Delta a^* \Delta b^*$ colorimetric difference value. This difference value is used for quantitative comparisons of absolute color in the ROI. As an alternative, the entire matched images can be averaged, converted to colorimetric values, and subtracted, instead of just the ROI. However, this requires more processing.

As an example, FIG. 4 illustrates an exemplary training image 410 which is to be compared to an exemplary monitored image 420, in accordance with the method 200 of FIGS. 2A-2B. The training image 410 and the monitored image 420 are a matched pair of aligned color images which are a result of steps 210-232 of the method 200. The matched pair of images 410 and 420 correspond to a vertical section of the printed outside surface of a common, substantially cylindrical soda can. The pixels making up the two images 410 and 420 are represented as RGB data (i.e., the characteristic parameter is RGB color data).

FIG. 5 illustrates an exemplary comparison image 500 generated by subtracting the reference image 410 of FIG. 4 from the monitored image 420 of FIG. 4 on a pixel-by-pixel basis, in accordance with the method 200 of FIGS. 2A-2B. The resultant comparison image is typically offset or scaled as described below. The comparison image 500 is a result of step 233 of the method 200. In step 233, the pixel values of the resultant comparison image 500 are $\Delta R \Delta G \Delta B$ data values. The comparison image 500 indicates any difference between the training image 410 and the monitored image 420. A subtle difference in RGB color (i.e., $\Delta R \Delta G \Delta B$ data values) 501 is seen in the comparison image 500 which may be due to a deviation in one of the colors of ink used to print the soda can. Also, a not so subtle difference 502 is seen which may be due to, for example, a scratch or flaw being introduced on the surface of the soda can after printing by some part of the process line.

In step 240, at least one process deviation signal is generated from the comparison image data. For example, the values $\Delta R \Delta G \Delta B$ of the comparison image 500 of FIG. 5 are converted to $\Delta E$ (Euclidean distance) values for each pixel of the comparison image as $$\Delta E = \sqrt{(\Delta R^*)^2 + (\Delta G)^2 + (\Delta B^*)^2}$$

Each $\Delta E$ value for each pixel is compared to a predetermined threshold. A count value is generated corresponding to the number of comparison image pixels whose $\Delta E$ values are greater than (or, alternatively, less than) the predetermined threshold. This count value is output as the process deviation signal 125 (see FIG. 1) by the computer based platform 120 and may indicate a pass or a fail condition when compared to another predetermined pass/fail threshold. The process deviation signal 125 may be used as an input to an adaptive process control system 130 to bring the process back into spec (see FIG. 1).

In accordance with an embodiment of the present invention, the $\Delta R \Delta G \Delta B$ values are scaled such that comparison image difference values of zero correspond to a value of 128 on a RGB color scale of 0-255. As a result, both positive (greater than 128) and negative (less than 128) $\Delta R \Delta G \Delta B$ values are accommodated on the 0-255 RGB color scale, which represents 256 distinct color differences.

For quantitative colorimetric evaluation, $\Delta X \Delta Y \Delta Z$ or $\Delta L^* \Delta a^* \Delta b^*$ colorimetric data can be used to calculate a Euclidean distance for averaged pixels in a region of interest as, for example, $$\Delta E = \sqrt{(\Delta L^*)^2 + (\Delta a^*)^2 + (\Delta b^*)^2}$$

The pixels in a ROI are averaged, forming an average characteristic parameter value (e.g., average RGB color value), and converted to a L*a*b* calorimetric value, for example. This is done for both the training image and the corresponding aligned monitored image. The difference is taken and constitutes a process deviation signal or value (e.g., $\Delta L^* \Delta a^* \Delta b^*$ value) which can be used as an input to an adaptive process control system 130 to adjust color.

As a matter of practicality, not every soda can passing by the vision system 100 on the process line may be properly imaged (i.e., some images may be of poor quality and need to be discarded) or matched to a training image (e.g., when the confidence measure is low). In such a process monitoring situation, it is not important to check and characterize every monitored object (e.g., every soda can). Instead, it is important to obtain a good sampling of the soda cans as they go by such that the process deviation signal 125 is monitored over time to make sure the process (e.g., color printing process of the soda cans) is not getting out of control. For example, in accordance with an embodiment of the present invention, the process deviation signal 125 may be a running average of the count value described above. Other process deviation value signals are possible as well, in accordance with various embodiments of the present invention.

Figure 6A:
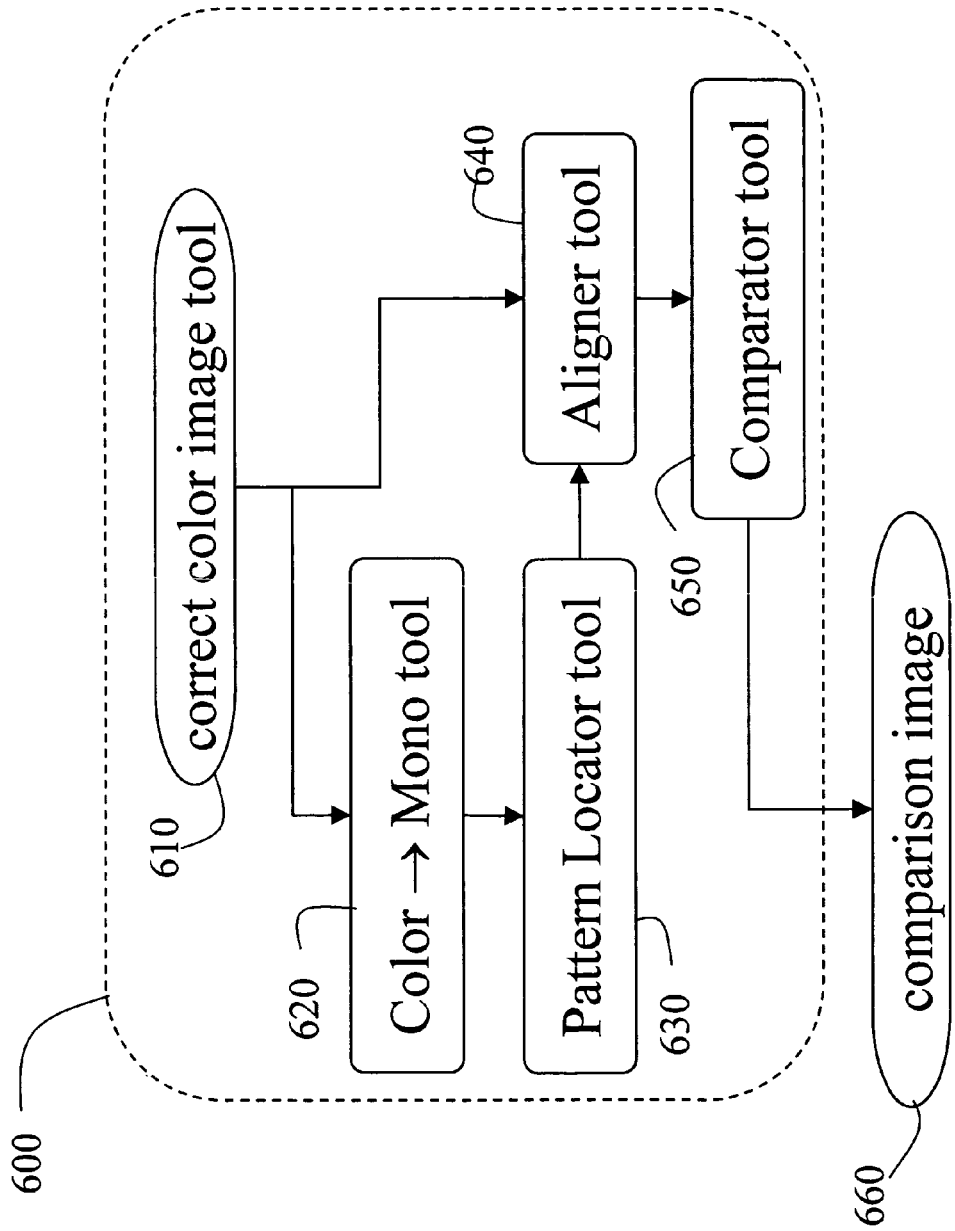
FIG. 6A illustrates a schematic block diagram of a set of software tools used by a computer-based platform of the vision system of FIG. 1 to process image information, in accordance with an embodiment of the present invention.

FIG. 6A illustrates a schematic block diagram of a set of software tools 600 used by a computer-based platform 120 of the vision system 100 of FIG. 1 to process image information, in accordance with an embodiment of the present invention. The set of software tools 600 includes a correct color image tool 610, a color-to-mono tool 620, a pattern locator tool 630, an aligner tool 640, and a comparator tool 650. The output of the comparator tool is the comparison image 660. These tools may include commercial, off-the-shelf tools and/or customized tools in accordance with various embodiments of the present invention.

Figure 6B:
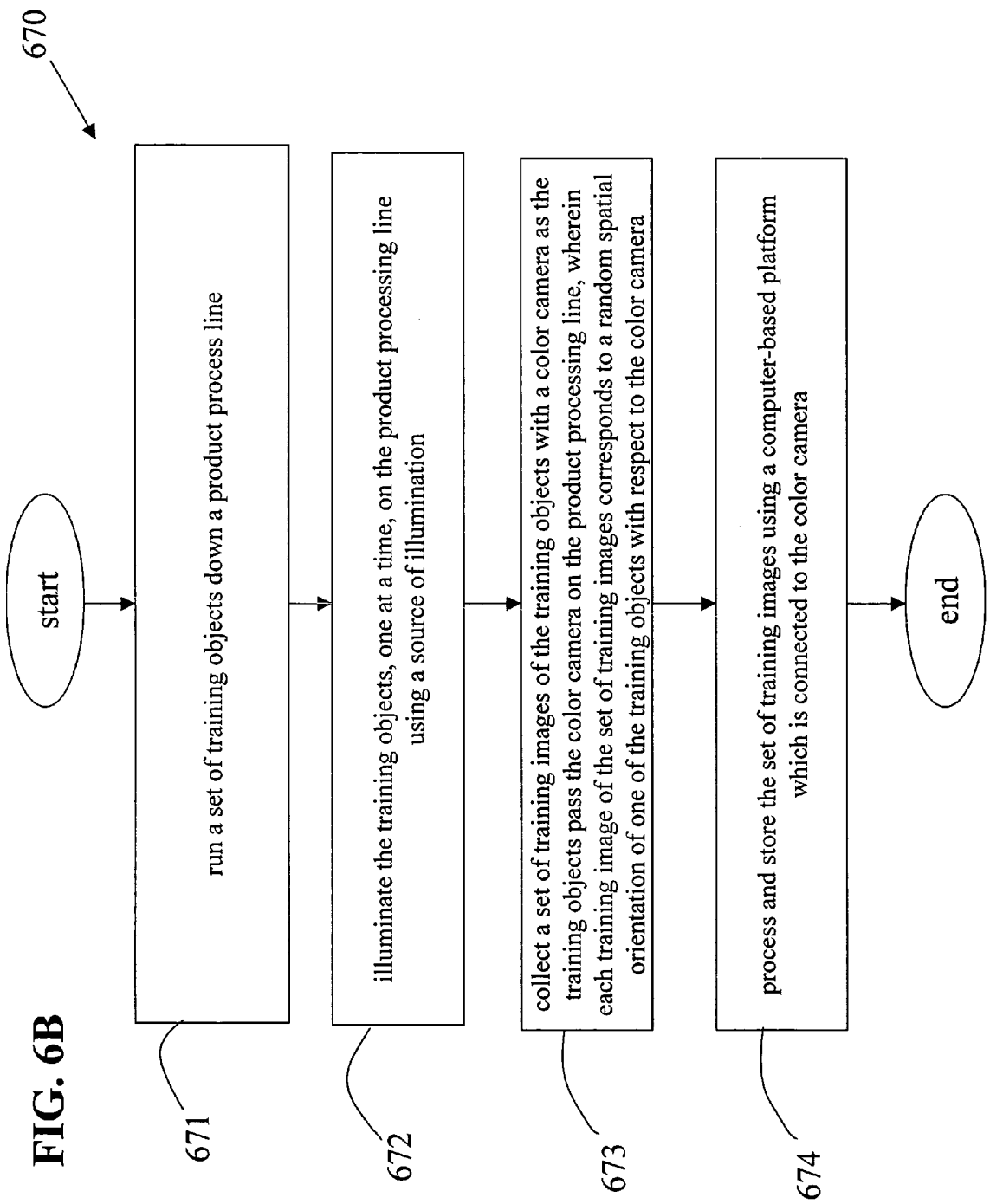
FIG. 6B is a flowchart of an embodiment of a method to train the vision system of FIG. 1 on-line, in accordance with various aspects of the present invention.

When training images are captured by the vision system 100, the training images are corrected for lighting non-uniformity by the correct color image tool 610. FIG. 6B is a flowchart of an embodiment of a method 670 to train the vision system of FIG. 1 on-line, in accordance with various aspects of the present invention. In step 671, a set of training objects is run down a product processing line. In step 672, the training objects are illuminated, one at a time, on the product processing line using a source of illumination. In step 673, a set of training images of the training objects is collected with a color camera as the training objects pass the color camera on the product processing line, wherein each training image of the set of training images corresponds to a random spatial orientation of one of the training objects with respect to the color camera. In step 674, the set of training images are processed and stored using a computer-based platform which is connected to the color camera.

In accordance with an embodiment of the present invention, sixteen (16) training images are acquired to form a training set. An operator of the vision system may view the sixteen (16) training images on, for example, a display. If he so desires, the operator may delete any or all of the training images from the training set. He may also collect additional training images on-line to replace those images that he has deleted. An operator may be motivated to delete images if two or more images appear to be substantially redundant, if an image appears to be corrupted, or if there is simply not much going on in a particular image (i.e., not much detail or variation).

Similarly, when monitored images are captured by the vision system 100, the monitored images are corrected for lighting non-uniformity by the correct color image tool 610. FIG. 6C is a flowchart of an embodiment of a method 680 to monitor a process, in accordance with various aspects of the present invention. In step 681, one monitored image is acquired from each of at least one randomly oriented object to be monitored on a process line over a period of time using a vision system. Each of the objects to be monitored is expected to be substantially similar to a set of training objects. In step 682, at least one acquired monitored image of the at least one object to be monitored is compared to a set of stored training images of the training objects to form at least one comparison image of comparison values. In step 683, at least one process deviation signal is generated in response to the comparing step.

As a pre-processing step to pattern location, the training images and a monitored image to be compared may be converted from color to monochrome (e.g., to a gray scale pattern or a simple edge pattern), using the color-to-mono tool 620 to make the pattern locator process simpler. The pattern locator tool 630 takes the monitored image and tries to match its pattern to that of one of the training images.

Figure 7:
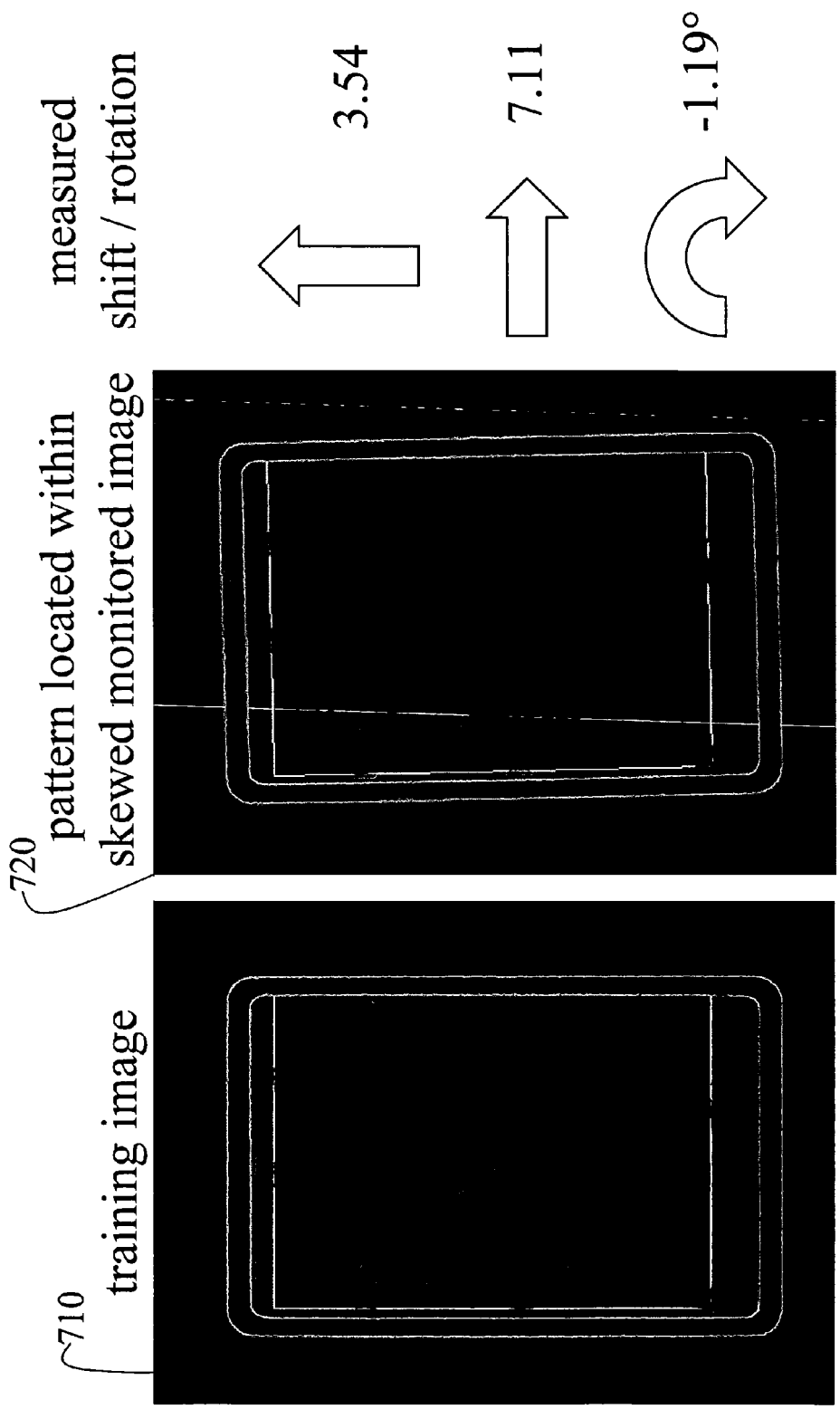
FIG. 7 illustrates the concept of pattern matching performed by the pattern locator tool of FIG. 6A as part of the method step of FIG. 2B, in accordance with an embodiment of the present invention.

FIG. 7 illustrates the concept of pattern matching performed by the pattern locator tool 630 of FIG. 6A as part of the method step 231 of FIG. 2B, in accordance with an embodiment of the present invention. A monitored image 720 is compared to a training image 710 and a pattern match is achieved. However, the matched pattern of the monitored image 720 is spatially skewed with respect to the training image 710. For example, the matched pattern of the monitored image 720 is 3.54 pixels too high, 7.11 pixels too far to the right, and rotated −1.19 degrees with respect to a pixel coordinate system of the training image 710.

Figure 8:
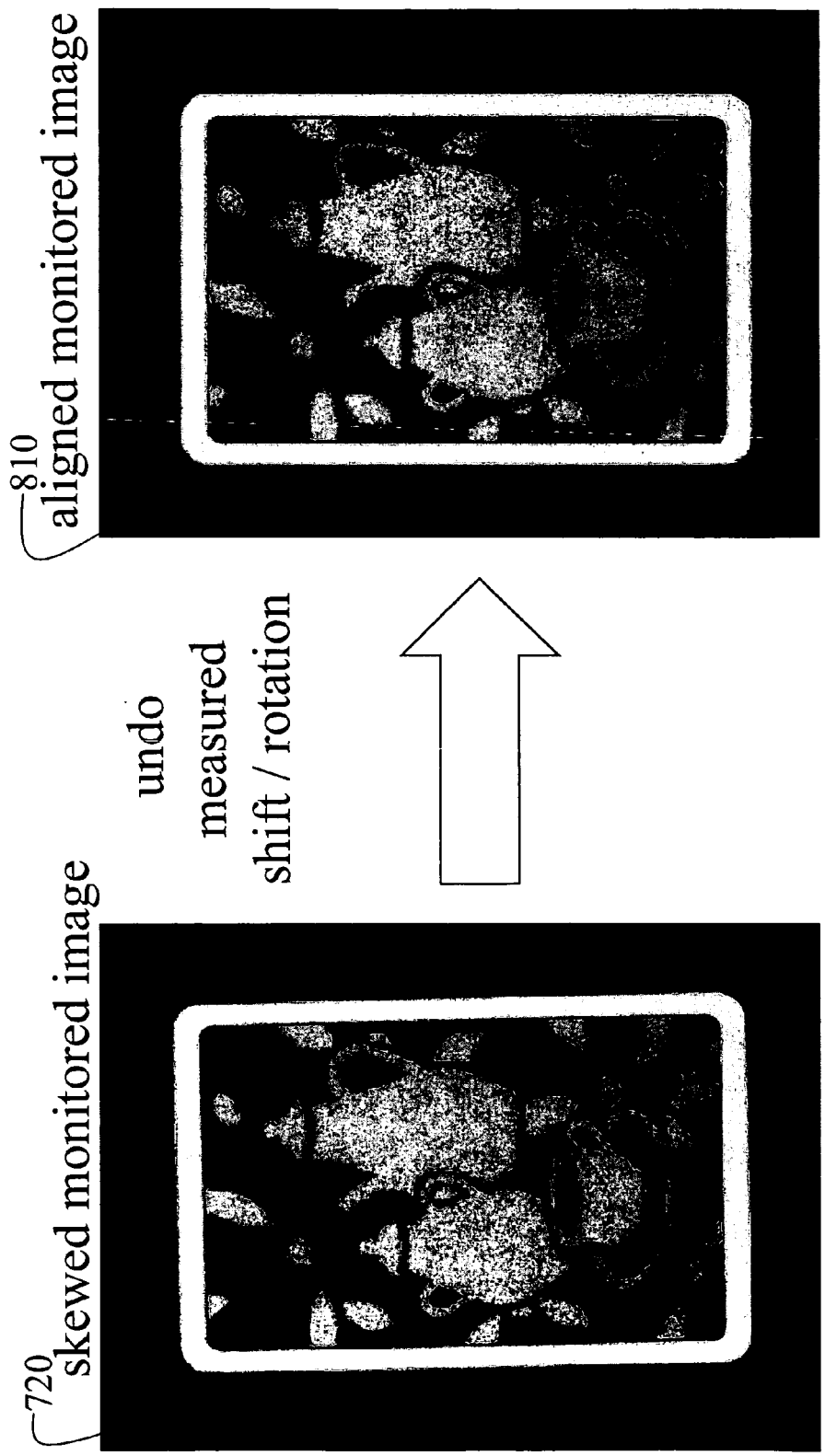
FIG. 8 illustrates the concept of spatial alignment performed by the aligner tool of FIG. 6A as part of the method step of FIG. 2B, in accordance with an embodiment of the present invention.

The aligner tool 640 is used to align the monitored image 720 to the training image 710 based on the skew parameters (3.54, 7.11, −1.19°) calculated as part of the pattern matching process. FIG. 8 illustrates the concept of spatial alignment performed by the aligner tool 640 of FIG. 6A as part of the method step 232 of FIG. 2B, in accordance with an embodiment of the present invention. The skewed monitored image 720 is transformed to an aligned image 810 (i.e., undoing the measured shift and rotation) by the aligner tool 640. The alignment operation is performed on the color monitored image (not the corresponding monochrome image used for pattern matching).

Whether doing qualitative comparisons on RGB data or quantitative comparisons on colorimetric data, an aligned image is used for comparison to the training image or a region of interest of the training image.

Figure 9:
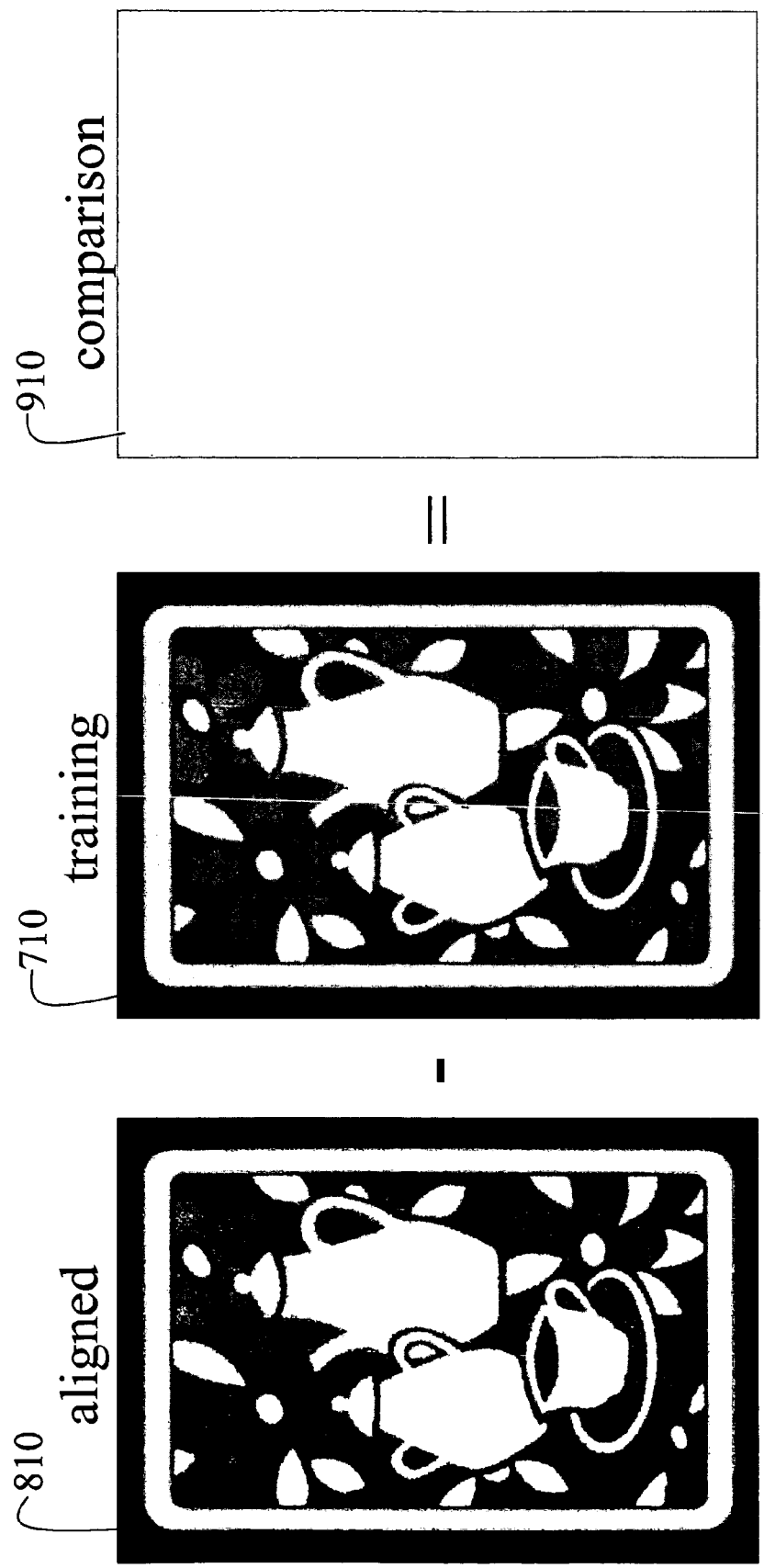
FIG. 9 illustrates the concept of generating a comparison image using the comparator tool of FIG. 6A as part of the method step of FIG. 2B, in accordance with an embodiment of the present invention.

FIG. 9 illustrates the concept of generating a comparison image 910 using the comparator tool 650 of FIG. 6A as part of the method step 233 of FIG. 2B, in accordance with an embodiment of the present invention. A comparison image 910 of pixels is formed in step 233 of the method 200 by, for example, performing a subtraction of the RGB values of corresponding aligned pixels to obtain a comparison image 910 of $\Delta R \Delta G \Delta B$ values. The resultant comparison image is typically offset or scaled as previously described.

Alternatively, a comparison image 910 of pixels is formed in step 233 of the method 200 by, for example, first converting the RGB pixel values of the matched pair of images to XYZ or L*a*b* calorimetric data using a color transformation algorithm. The resultant comparison image comprises $\Delta X \Delta Y \Delta Z$ or $\Delta L^* \Delta a^* \Delta b^*$ colorimetric data as previously described.

Also, a ROI of RGB data can be averaged for the training image and the matched monitored image, converted to calorimetric data, and then subtracted to form a calorimetric difference value (i.e., a process deviation signal) as in the method 300 of FIGS. 3A-3B.

In practical applications, both a $\Delta R \Delta G \Delta B$ comparison image and a $\Delta X \Delta Y \Delta Z$ or $\Delta L^* \Delta a^* \Delta b^*$ comparison value, based on a region of interest (ROI), are generated. The $\Delta R \Delta G \Delta B$ comparison image is used for a qualitative assessment of the process and the $\Delta X \Delta Y \Delta Z$ or $\Delta L^* \Delta a^* \Delta b^*$ comparison value is used for quantitative assessment of color.

As described before, a process deviation signal 125 may be generated using thresholding and counting techniques, or other techniques as well, in accordance with various embodiments of the present invention. Again, the process deviation signal 125 may be used as an input to an adaptive process control system 130 to bring the process back into control. Alternatively, the process deviation signal may be used by an operator to manually adjust the process.

FIG. 10 is a flowchart of an embodiment of a method 1000 for training and monitoring an industrial can or container process, in accordance with various aspects of the present invention. In step 1010, a set of training images from at least two training cans is acquired on a process line using a vision system. Each training image of the set of training images corresponds to a random rotational orientation of one of the training cans on the process line with respect to the vision system. In step 1020, one monitored image from at least one randomly rotationally oriented monitored can is acquired on the process line over a period of time using the vision system. Each monitored can is expected to be substantially similar to the training cans. In step 1030, at least one acquired monitored image of the at least one monitored can is compared to the set of training images of the training cans to form at least one comparison image of comparison values or region of interest of comparison values. In step 1040, at least one process deviation signal is generated in response to the comparing step.

In summary, a method and system to monitor randomly oriented objects on a production process line are disclosed. A color camera is used initially to collect a set of training images of a set of training objects as the training objects pass by the color camera on a process line. The training images represent various random spatial orientations of the training objects with respect to the color camera. The training objects serve as the standard for the process. The training images are stored in a computer-based platform. The color camera is then used to capture images of monitored objects as the monitored objects pass by the color camera on a process line. The monitored objects have a random spatial orientation with respect to the color camera as the monitored objects pass through the field-of-view of the color camera. The captured images of the monitored objects are processed by the computer-based platform and compared to the training images in order to determine if certain characteristic parameters of the monitored objects have deviated from those same characteristic parameters of the training objects. If so, the process may be adjusted to correct for the deviations in order to bring the process back into tolerance.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method for training and monitoring a process, said method comprising:

acquiring a set of training images from a portion of a substantially cylindrical side of each of a plurality of training objects on a processing line using a vision system, wherein each training image of said set of training images corresponds to a random spatial orientation of said training objects with respect to said vision system as said training objects pass by said vision system on said processing line;

acquiring one monitored image from a portion of a substantially cylindrical side of each of at least one randomly oriented object to be monitored coming down said processing line over a period of time using said vision system, wherein each object to be monitored is substantially similar to said training objects;

comparing at least one acquired monitored image of said at least one object to be monitored to said set of training images of said training objects to form at least one comparison image of comparison values or region of interest of comparison values; and generating at least one process deviation signal in response to said comparing.

2. The method of claim 1 wherein said comparing comprises:

attempting to pattern match each acquired monitored image to a training image of said set of training images;

spatially aligning each matched monitored image with a corresponding matched training image; and subtracting at least one characteristic parameter of a plurality of aligned pixels of said matched training image from at least one characteristic parameter of a plurality of corresponding aligned pixels of said corresponding matched monitored image, for each matched pair of monitored and training images, to form said at least one comparison image or region of interest of comparison values.

3. The method of claim 2 further comprising calculating said at least one characteristic parameter for said plurality of aligned pixels of said matched monitored image and said corresponding matched training image, for each matched pair of monitored and training images, before performing said subtraction.

4. The method of claim 2 wherein said at least one characteristic parameter comprises RGB color data.

5. The method of claim 3 wherein said at least one characteristic parameter comprises colorimetric data.

6. The method of claim 1 wherein said at least one process deviation signal comprises a pass/fail value.

7. The method of claim 1 wherein said at least one process deviation signal comprises colorimetric data.

8. The method of claim 1 further comprising feeding back said at least one process deviation signal to a process control system to correct for a deviation in said process.

9. The method of claim 1 wherein said generating said at least one process deviation signal comprises counting every pixel in said at least one comparison image or said region of interest having a comparison value greater than or less than a first predetermined threshold value.

10. The method of claim 1 further comprising correcting said set of training images and each of said monitored images for non-uniform lighting before said comparing step.

11. A vision system for training and monitoring a process, said vision system comprising:

a source of illumination positioned to illuminate a portion of a substantially cylindrical side of objects for training and a portion of a substantially cylindrical side of objects to be monitored, as said training objects and said objects to be monitored move along a process line in spatially random orientations;

a color camera positioned on said process line to capture at least one image from each of said illuminated portion of said training objects and each of said illuminated portion of said objects to be monitored, forming a plurality of training images and a plurality of monitored images, as each training object and each object to be monitored passes through a field-of-view of said color camera; and
a computer-based platform being connected to said color camera to store said plurality of training images and said plurality of monitored images and to generate at least one process deviation signal by comparing at least one monitored image of said plurality of monitored images to said plurality of training images.

12. The vision system of claim 11 wherein said computer-based platform includes a frame grabber to convert analog signals, output from said color camera, to digital signals representing single frames of digital imaging data.

13. The vision system of claim 11 wherein said plurality of training images correspond to random rotational positions of said plurality of training objects with respect to said color camera as said training objects move along said process line past said color camera, and wherein said objects to be monitored are substantially similar to said plurality of training objects.

14. The vision system of claim 11 wherein said source of illumination comprises an array of light emitting diodes which emits a spectrum of white light.

15. The vision system of claim 11 wherein said color camera outputs analog imaging signals.

16. The vision system of claim 11 wherein said color camera outputs digital imaging signals.

17. The vision system of claim 11 wherein said at least one process deviation signal comprises at least one of a pass/fail value and colorimetric data.

18. The vision system of claim 11 wherein said comparing, performed by said computer-based platform, comprises:
attempting to pattern match each of said plurality of monitored images to at least one training image of said plurality of training images;
spatially aligning each matched monitored image with a corresponding matched training image; and
subtracting at least one characteristic parameter of a plurality of aligned pixels of said matched training image from said at least one characteristic parameter of a plurality of corresponding aligned pixels of said corresponding matched monitored image, for each matched pair of monitored and training images, to form at least one comparison image of difference values or region of interest of difference values.

19. The vision system of claim 18 wherein said at least one characteristic parameter is calculated for said plurality of aligned pixels of said matched monitored image and said corresponding matched training image, before said subtracting, for each matched pair of monitored and training images.

20. The vision system of claim 18 wherein said at least one characteristic parameter comprises RGB color data.

21. The vision system of claim 18 wherein said at least one characteristic parameter comprises colorimetric data.

22. The vision system of claim 18 wherein said at least one process deviation signal is generated by counting every pixel in said at least one comparison image or region of interest having a difference value greater than or less than a first predetermined threshold value.

23. The vision system of claim 11 wherein said at least one process deviation signal is used to correct a deviation in said process.

24. A method for training and monitoring a process, said method comprising:
generating a set of training images from a portion of a substantially cylindrical side of each of a plurality of training objects on a product line using a vision system, wherein each training image of said set of training images corresponds to a random spatial orientation of each of said training objects on said product line with respect to said vision system;
acquiring one monitored image from a portion of a substantially cylindrical side of each of at least one randomly oriented object to be monitored on said product line over a period of time using said vision system, wherein each object to be monitored is substantially similar to said training objects; and
comparing at least one acquired monitored image of said at least one object to be monitored to said set of training images of said training objects to form at least one process deviation signal.

25. The method of claim 24 wherein said comparing comprises:
attempting to pattern match each acquired monitored image to a training image of said set of training images;
spatially aligning each matched monitored image with a corresponding matched training image;
averaging at least one characteristic parameter of a plurality of aligned pixels of said matched training image to form a first average characteristic parameter value, for each matched pair of monitored and training images;
averaging said at least one characteristic parameter of said plurality of corresponding aligned pixels of said corresponding matched monitored image to form a second average characteristic parameter value, for each matched pair of monitored and training images;
calculating a first colorimetric parameter value from said first average characteristic parameter value, for each matched pair of monitored and training images;
calculating a second colorimetric parameter value from said second average characteristic parameter value, for each matched pair of monitored and training images; and
subtracting said first colorimetric parameter value from said second colorimetric parameter value to form said at least one process deviation signal, for each matched pair of monitored and training images.

26. The method of claim 25 wherein said at least one characteristic parameter comprises RGB color data.

27. A method for monitoring a process, said method comprising:
acquiring one monitored image from a portion of a substantially cylindrical side of each of at least one randomly oriented object to be monitored on a process line over a period of time using a vision system, wherein each of said at least one object to be monitored is substantially similar to a set of training objects;
comparing at least one acquired monitored image of said at least one object to be monitored to a set of stored training images of said training objects to form at least one comparison image of comparison values; and
generating at least one process deviation signal in response to said comparing.

28. A method of training a vision system, said method comprising:
running a set of training objects down a product processing line;
illuminating a portion of a substantially cylindrical side of said training objects, one at a time, on said product processing line using a source of illumination;
collecting a set of training images of said portion of said side of said training objects with a color camera as said training objects pass said color camera on said product processing line, wherein each training image of said set of training images corresponds to a random spatial orientation of one of said training objects with respect to said color camera; and processing and storing said set of training images using a computer-based platform which is connected to said color camera.

29. The method of claim 28 further comprising:

viewing said training images on a display of said vision system;

deleting at least one of said training images from said set of training images; and training said vision system again to replace only said deleted training images with updated training images.

30. A method for training and monitoring an industrial can or container process, said method comprising:

acquiring a set of training images from at least two training cans on a process line using a vision system, wherein each training image of said set of training images corresponds to a random rotational orientation of one of said training cans on said process line with respect to said vision system;

acquiring one monitored image from at least one randomly rotationally oriented monitored can on said process line over a period of time using said vision system, wherein each monitored can is expected to be substantially similar to said training cans;

comparing at least one acquired monitored image of said at least one monitored can to said set of training images of said training cans to form at least one comparison image of comparison values or region of interest of comparison values; and generating at least one process deviation signal in response to said comparing.

* * * * *